United States Patent [19]

Ahn et al.

[11] Patent Number: 5,148,025
[45] Date of Patent: Sep. 15, 1992

[54] IN SITU COMPOSITION ANALYSIS DURING GROWTH VAPOR DEPOSITION

[76] Inventors: Channing C. Ahn, 3055 Oneida St., Pasadena, Calif. 91107; Harry A. Atwater, 390 Redwood Dr., Pasadena, Calif. 91105

[21] Appl. No.: 643,523

[22] Filed: Jan. 18, 1991

[51] Int. Cl.⁵ .................... H01J 47/00; H01J 37/00
[52] U.S. Cl. ............................. 250/305; 250/306; 250/307
[58] Field of Search ............... 250/305, 306, 307, 310

[56] References Cited

U.S. PATENT DOCUMENTS

| | | | |
|---|---|---|---|
| 3,612,859 | 10/1971 | Schumacher | 250/307 |
| 4,393,311 | 7/1983 | Feldman et al. | 250/310 |
| 4,812,650 | 3/1989 | Eckstein et al. | 250/307 |
| 4,829,022 | 5/1989 | Kobayashi et al. | 437/110 |
| 4,931,132 | 6/1990 | Aspnes et al. | 427/255.1 |

OTHER PUBLICATIONS

Ahn et al., "Reflection Electron Energy Loss Spectroscopy During Initial Stages of GE Heteroepitaxy on SI(001) by Molecular Beam Epitaxy", Abstract submitted to *Materials Research Society* for 1990 Fall Meeting, Jun. 1990 (1 page).

Atwater et al., "Reflection Electron Energy Loss Spectroscopy during Initial Stages of GE Growth on SI by Molecular Beam Epitaxy", Submitted Jul. 1990 for publication in *Appl. Phys. Lett.* 58 (3), 21 Jan. 1991, (9 pages+4 pages of Figures).

Ahn et al., "Electron Energy Loss Spectrometry of Surfaces and Interfaces", Abstract submitted Jun. 1990 for presentation at *The American Ceramic Society, Inc.* 43rd Pacific Coast Regional Meeting Oct. 25–27, 1990, (p. 11).

Ahn, Channing, "Electron Energy Loss Spectrometry of Surfaces During MBE Growth", Abstract submitted Jun. 1990 for presentation at *Exxon Research and Engineering Company* in Annandale, N.J. in Dec. 1990, (1 page).

Ahn et al., "Reflection Electron Energy Loss Spectroscopy During Initial Stages of GE Heteroepitaxy on SI (001) by Molecular Beam Epitaxy", view graphs presented at 1990 Fall Meeting of *Materials Research Society*, Nov. 1990 (3 pages).

Ahn et al., "Surface Analysis During the Growth of GE and $GE_xSI_{1-x}$ Alloys on SI by Reflection Electron Energy Loss Spectrometry", Submitted Jan. 1991 for publication in 1991 in *Material Research Society Symposium Proceedings* (Advances in Surface and Thin Film Defraction), (10 pages).

*Primary Examiner*—Bruce C. Anderson
*Attorney, Agent, or Firm*—Brunell & May

[57] ABSTRACT

The composition of material being grown by vapor deposition may be analyzed in situ by applying a beam of electrons, from a source such as a RHEED gun, incident at a low angle to the material being grown. The energy levels in the reflected beam may be analyzed by spectroscopy to qualitatively and quantitatively the presence and absence of elements, as well as their ratio, by analysis of the number of electrons at energy levels related to core level transitions representative of specific materials. Such compositional analysis may be used in real time to control the deposition growth process.

6 Claims, 2 Drawing Sheets

P     S X A        P     S B A

IN SITU COMPOSITION ANALYSIS DURING GROWTH VAPOR DEPOSITION

ORIGIN OF THE INVENTION

The invention was made with Government support under NSF 55251 awarded by the National Science Foundation. The Government has certain rights in the invention.

BACKGROUND OF THE INVENTION

1. Field of the Invention.

This invention relates to techniques for growing materials by vapor deposition, including physical vapor deposition, or PVD, and chemical vapor deposition, or CVD, techniques. In particular, this invention relates to the measurement and/or control of the composition of materials grown by vapor deposition techniques, including those used in the fabrication of integrated circuits by molecular beam epitaxy, or MBE.

2. Description of the Prior Art.

Diffraction techniques are commonly used for measuring the structure of materials, including those grown by vapor deposition. In particular, reflection high energy electron diffraction, or RHEED, techniques are commonly used for in situ measurements of the structure of a layer being grown by MBE in the fabrication of integrated circuits.

In the RHEED technique, a beam of high energy electrons, on the order of 10 keV or greater, are incident at a small angle on the surface of the layer being grown. The diffracted and reflected beams strike a target, such as a phosphor screen. The resultant pattern on the target may be used to determine the structure of the crystalline surface from which the electrons were reflected and diffracted.

Electron energy loss spectroscopy, or EELS, techniques are used for analysis of the composition of materials, such as semiconductor layers grown by MBE. EELS techniques include transmission spectroscopy in which a beam of highly collimated electrons is applied to one side of a thin layer of a material to be analyzed. The energy states of the electrons emerging from the other side of the material are analyzed. Transmission electron spectroscopy equipment has also been used in diffraction experiments in which the collimated electron beam has been applied to a target surface for composition analysis by diffraction.

Reflection electron energy loss spectroscopy, or REELS, techniques are also utilized for the analysis of material composition. The energy states of the scattered incident electrons reflected from the target surface are analyzed to determine the composition of the target. REELS techniques can be used with PVD processes and may be used with CVD processes that employ a sufficiently low operating pressure to permit passage of the incident electron beam through the gas phase in the deposition chamber.

Other surface analysis techniques include Auger spectroscopy and X-ray photoelectron spectroscopy techniques in which a beam of electrons or X-rays strikes the surface of a target layer and knocks electrons out of that target surface for analysis.

Conventional spectroscopy techniques may be used to provide valuable information about the composition of materials that have been grown by vapor deposition, but they do not provide in situ composition information during the growth of materials in deposition chambers. Such conventional techniques, unlike the above describe REELS techniques, often require short working distances, that is, the collector must be positioned extremely close to the surface of the target. This is not convenient for use with deposition techniques in which the arrangement and composition of the materials within the deposition chamber must be tightly controlled.

What is needed is a long working distance technique for the in situ analysis of the composition of materials being grown by vapor deposition. The needed technique must permit the analysis equipment to be positioned well away from the growth substrate. In addition, the technique should permit real time analysis, that is, the analysis time should be short enough so that composition information may be used in a feedback loop to control the composition of the material being grown.

SUMMARY OF THE INVENTION

The preceding and other shortcomings of the prior art are addressed and overcome by the present invention that provides a method of analyzing materials by applying a beam of electrons incident upon material being grown by vapor deposition, and analyzing the material in accordance with electron energy levels in the scattered incident electron beam reflected therefrom.

In another aspect, the invention provides apparatus for analyzing materials with means for applying a beam of electrons incident upon a material being grown by vapor deposition, and means for analyzing the material in accordance with electron energy levels in the scattered incident electron beam reflected therefrom.

These and other features and advantages of this invention will become further apparent from the detailed description that follows which is accompanied by one or more drawing figures. In the figures and description, numerals indicate the various features of the invention, like numerals referring to like features throughout both the drawing figures and the description.

BRIEF DESCRIPTION OF THE DRAWING(S)

FIG. 1 is a block diagram outline of a composition analysis technique according to the present invention useful for the real time, in situ evaluation of materials during growth in a deposition chamber.

FIG. 2 is an illustration of pattern 34 on RHEED target 28 resulting from reflected electron beam 30, as shown in FIG. 1.

FIGS. 3a–d are a series of graphs which present idealized representations of the output of spectroscopy system 40, shown in FIG. 1.

FIGS. 4a–d are a series of graphs indicating stages in the growth of a compound layer of material A and material B being grown in a ratio of 2:1 on a substrate of material S.

DETAILED DESCRIPTION OF THE PREFERRED EMBODIMENT(S)

Figure 1:
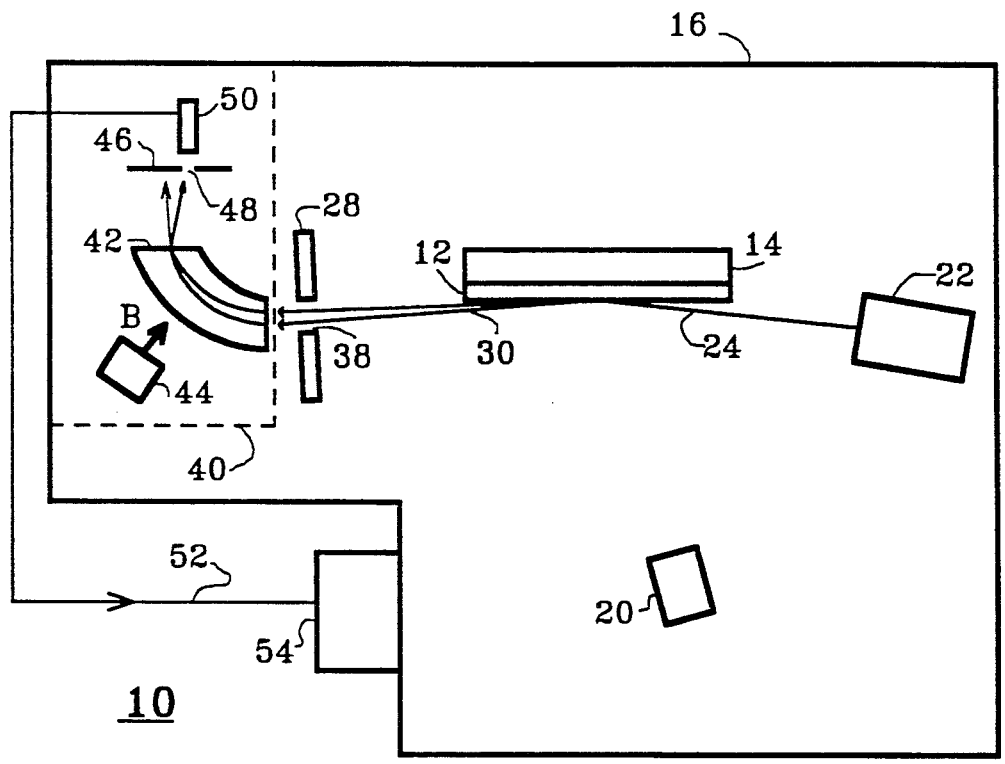

FIG. 1 is a block diagram of composition analysis system 10 being used for the real time, in situ evaluation of the composition of layer 12 being grown on substrate 14 in deposition chamber 16. In the particular growth by vapor deposition example shown in this figure, material from deposition source 20 will be deposited on substrate 14, forming layer 12.

For analysis purposes, a source of electrons such as RHEED gun 22 applies incident electron beam 24 to strike layer 12 at a relatively shallow angle. Conventional RHEED target 28 may be positioned to intersect reflected electron beam 30. As described so far, RHEED gun 22 and RHEED target 28 form the major components of a conventional RHEED system which is commonly used for the in situ analysis of the structure of layer 12 during growth in deposition chamber 16.

Figure 2:
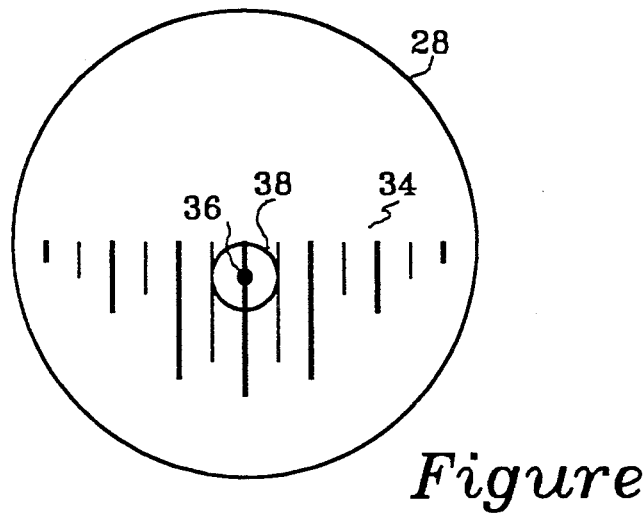

Referring now to FIG. 2, pattern 34 is formed by reflected electron beam 30 on RHEED target 28 as a result of the diffraction of incident electron beam 24 by the crystal structure of layer 12. Pattern 34 includes specular beam 36 which results from the portion of incident electron beam 24 which is reflected by layer 12 but not substantially diffracted thereby. Pattern 34 is conventionally used for the analysis of the structure of layer 12 during its growth in deposition chamber 16.

However, in accordance with the present invention, variations in the energies of the electrons in reflected electron beam 30 are also analyzed in order to determine the composition of layer 12 during growth in deposition chamber 16. Incident electron beam 24 is reflected inelastically from the surface of layer 12 with electron energy losses indicative of the composition of layer 12.

The dominant effect causing energy loss for electrons striking a crystalline surface is thought to result from plasmons, that is, interaction of the electron beam with the electrons in place as if in a plasma in the material. The magnitude of this energy loss is relatively low and it is not presently possible to distinguish composition information from such losses.

However, in addition to the plasmon effect, the incident electrons lose detectable amounts of energy as a result of energy transitions of electrons in the target material from the ground state to an excited state. Such transitions are called core level transitions. Although core level transitions are not the dominant cause of energy loss, the magnitudes of the energy losses due to core level transitions are much larger than those caused by plasmon effects and are specific to the elements in which the transitions are caused to occur. That is, the energy loss resulting from a core level transition in one element is distinguishable from the energy loss resulting from a core level transition in another element.

By analyzing reflected electron beam 30 to determine the presence or absence of electron energy losses indicative of core level transitions for a material of interest, it is possible to qualitatively determine the presence of that element in layer 12. For example, if layer 12 of germanium was to be grown on silicon substrate 14, electrons in reflected electron beam 30 having energy losses indicative of core level transitions in silicon would be detectable at the beginning of the growth process.

After germanium layer 12 was grown sufficiently thick on silicon substrate 14 so that electrons in incident electron beam 24 were no longer able to penetrate layer 12 to reach the silicon atoms, electrons having energy losses indicative of core level transitions in silicon would not be present in reflected electron beam 30. Electrons in reflected electron beam 30 having energy losses indicative of core level transitions in germanium layer 12 would, however, be present. Detection of electrons at such energy levels in reflected electron beam 30 therefore provides information concerning the composition of the material, either substrate 14 or layer 12, upon which the electrons in incident electron beam 24 are incident.

In addition to the simple qualitative composition analysis described above, more sophisticated quantitative analyses may be performed as will be described below in greater detail with respect to FIG. 3. The techniques for detecting and analyzing electron energy losses in a reflected beam, such as reflected electron beam 30, will first be discussed in greater detail with respect to spectroscopy system 40 shown in FIG. 1.

By removal of RHEED target 28, or by providing an aperture such as opening 38 through RHEED target 28 as shown in FIGS. 1 and 2, the energy levels of the electrons in reflected electron beam 30 may be analyzed by any appropriate conventional technique, such as by spectroscopy system 40. Spectroscopy, as used in EELS or REELS systems, provides a convenient technique for observing the energy spectrum of the electrons in reflected electron beam 30, whether or not such electrons have also been diffracted.

After passing through opening 38, reflected electron beam 30 enters passageway 42 in spectroscopy system 40 where it is subjected to a strong magnetic field applied transverse to the direction of electron travel from an appropriate source, such as magnet 44. The magnitude of the field applied by magnet 44 to reflected electron beam 30 within passageway 42 may be adjusted so that the paths of the electrons are bent differing amounts in accordance with their differing electron energies. In this manner, a portion of the electrons in reflected electron beam 30 having a particular energy loss, resulting for example from core level transitions indicative of the material of interest being grown as layer 12, may be differentiated from other electrons within reflected electron beam 30 having different energy levels.

Slit 46, including target window 48, may be positioned so that only electrons having a preselected energy level pass through target window 48. The magnetic field applied by magnet 44 may be altered to change the energy level selected by the position of target window 48. Those electrons with the selected energy level pass through target window 48 to strike an appropriate counter, such as scintillation counter 50, which is used to convert the electrons into signal 52, indicative of the number of electrons passing through target window 48 during a fixed time interval. In scintillation counter 50, the electrons strike a target, not shown, such as a plastic material which generates a photon when struck by an electron. The number of photons, and therefore the number of electrons passing through target window 48, may be counted with the aid of a photomultiplier, multiplier, or similar device not shown. In this manner, the composition of layer 12 may be determined by monitoring the presence in reflected electron beam 30 of electrons having energy levels representing losses due to core level transitions specific to the materials of interest.

If the intensity of incident electron beam 24 is high enough to provide a detectable number of electrons in reflected electron beam 30 in a relatively short time reflecting the appropriate core level transitions, the growth of layer 12 may be monitored, and/or controlled, in real time. In particular, signal 52 may be applied to deposition control subsystem 54 of deposition chamber 16. As a simple example, if spectroscopy system 40 is adjusted to detected electrons having energy losses indicative of core level transitions likely in silicon, the loss of signal 52 might be used to indicate that silicon substrate 14 had been appropriately covered by the growth of layer 12 of another material, such as germanium. Current experimental data indicates sensitivities in the range of layer thicknesses of about 1.5 nm to about 3 nm.

As noted above, quantitative as well as qualitative measurements of the composition of materials being grown by physical vapor deposition in deposition chambers may also be conveniently analyzed with the present invention. Referring now to FIG. 3, a series of graphs are presented which represent idealized displays of the output of spectroscopy system 40, as shown in FIG. 1. Each idealized signal display in FIGS. 3 and 4 represents an integrated intensity for a fixed energy window size. The pre-edge background intensity has been subtracted from each signal for clarity.

Figure 3A:
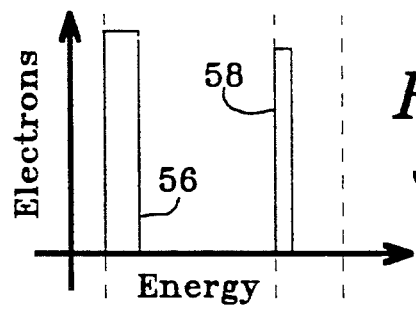

FIG. 3a represents the output of spectroscopy system 40 at the beginning of growth by vapor deposition of a layer of material A on a substrate of material S. Before a substantial amount of A has been grown on substrate S, substrate measurement 58 indicates a large number of electrons at one energy level. This energy level represents the number of electrons having core level transitions at an energy level related to the material of the substrate. In the following graphs, this energy level is indicated as energy level S, as shown at the bottom of FIG. 3, just below FIG. 3d.

As noted above, the dominant cause of energy loss in reflected electron beam 30 is due to the plasmon effect. Energy losses due to the plasmon effect are represented in the following graphs as plasmon energy measurement 56 at the energy level indicated as energy level P. The number of electrons detected at energy level S is substantially smaller than the number of electrons detected at energy level P.

Figure 3B:
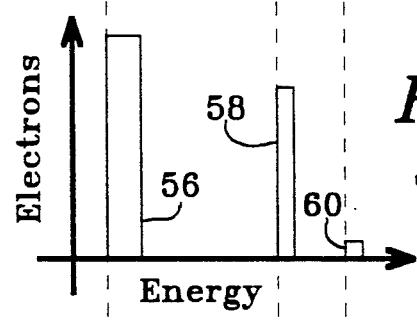

As the growth of layer A begins, incident electron beam 24 begins to strike some atoms of the material of layer A instead of atoms of substrate S. This is represented in FIG. 3b as a decrease in the magnitude of substrate measurement 58 and a corresponding increase, from zero, of layer measurement 60. Layer measurement 60 represents the number of electrons having core level transitions at an energy level related to the material of the layer being grown. This energy level is indicated as energy level A.

Figure 3C:
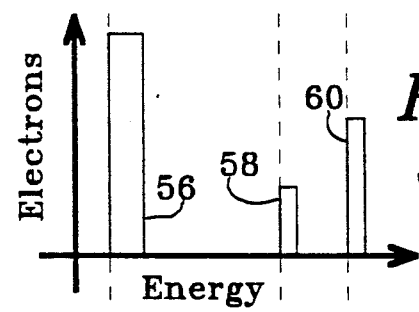

FIG. 3c represents a later stage during the growth of the layer. More and more electrons strike the atoms of the layer, while fewer electrons strike the atoms of the substrate. The total number of electrons causing core level transitions stays about the same, but layer measurement 60 increases at the expense of substrate measurement 58.

Figure 3D:
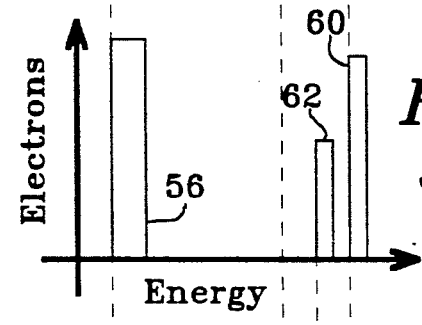

This progression increases until, as shown in FIG. 3d, substrate measurement 58 decreases to zero and layer measurement 60 increases to its value for an infinitely thick layer. At the point in time represented by FIG. 3d, the layer of material A is sufficiently thick to substantially shield the substrate from incident electron beam 24. Depending upon the particular materials being used, substrate measurement 58 may go to zero when the layer of material A is on the order of about 3 nm thick. The rate of growth between the times represented by FIG. 3a and 3d may be used to determine the final thickness of the layer.

In addition to providing information concerning the materials of the substrate and the layer being grown, the present invention may also provide information concerning the presence of unwanted contaminants. A measurement indicating the presence of electrons having energy losses at energy levels representative of materials not known to be present within the vapor deposition chamber, such as contamination measurement 62 shown in FIG. 3d at energy level X, indicates core level transitions occurring in a contaminant. The actual value of energy level X indicates the material of the contaminant.

The present invention may also be used for determining or monitoring the composition ratio of a compound layer being grown from multiple materials. FIG. 4 is a series of graphs indicating stages in the growth of a layer of material A and material B being grown in a ratio of 2:1 on a substrate of material S. At the time indicated by FIG. 4a, in addition to the electrons having energy losses indicating the plasmon effects shown as plasmon energy measurement 56, substrate measurement 64 indicates electron beam interaction with the substrate S. There are no noticeable amounts of electrons having losses at energy levels B or A. This indicates the absence of materials B and A at the beginning of the growth cycle.

Figure 4A:
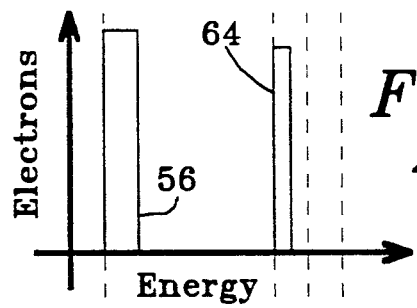
Figure 4B:
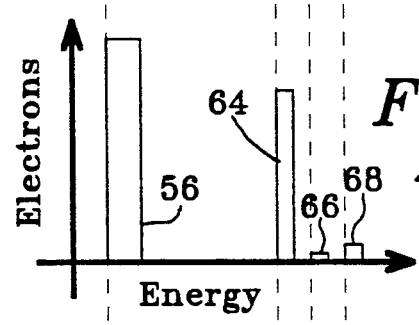

At the time represented by FIG. 4b, substrate measurement 64 is slightly reduced from its value in FIG. 4a. A small amount of materials A and B have been grown on substrate S as indicated by the presence of material B measurement 66 and material A measurement 68. The magnitude of material A measurement 68 is greater than the magnitude of material B measurement 66 which is consistent with the desired composition ratio of the layer being grown.

Figure 4C:
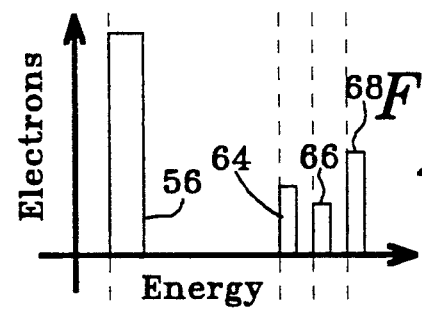

At the time represented by FIG. 4c, it can clearly be seen by the reduced magnitude of substrate measurement 64 that a substantial number of electrons are no longer reaching the substrate. The electrons are striking atoms of material A and material B in the layer being grown in numbers in the same ratio as the composition ratio in the layer, as indicated by the ratio of material A measurement 68 to material B measurement 66.

Figure 4D:
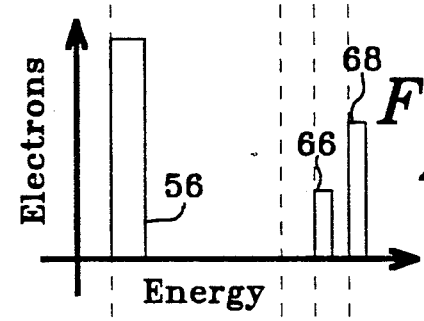

After a sufficient thickness of the layer has been grown so that electrons no longer reach the substrate, substrate measurement 64 becomes effectively zero as shown in FIG. 4d. As shown in that figure, material A measurement 68 is approximately twice the magnitude of material B measurement 66 indicating the proper ratio of materials in the layer. Continual measurement of this ratio during further growth of the layer may be used to control the composition ratio in the final layer.

While this invention has been described with reference to its presently preferred embodiments, its scope is not limited thereto. Rather, such scope is only limited in so far as defined by the following set of claims and includes all equivalents thereof.

What is claimed is:

1. A method of analyzing materials comprising the steps of:
    applying a beam of electrons incident upon material being grown by vapor deposition; and
    analyzing the material in accordance with electron energy levels in the scattered incident electron beam reflected therefrom.

2. The method of analyzing materials claimed in claim 1, wherein the material analysis step further comprises the step of:
    determining the presence or absence of a particular material in the material being grown in accordance with the presence or absence, in the reflected beam, of electrons at a predetermined energy level.

3. The method of analyzing materials claimed in claim 1, wherein the material analysis step further comprises the step of:

determining the composition ratio of materials present in the layer being grown in accordance with the ratio, in the reflected beam, of electrons at different predetermined levels.

4. Apparatus for analyzing materials, comprising:

means for applying a beam of electrons incident upon a material being grown by vapor deposition; and means for analyzing the material in accordance with electron energy levels in the scattered incident electron beam reflected therefrom.

5. The apparatus for analyzing materials claimed in claim 4, wherein the means for analyzing the material further comprises:

means for determining the presence or absence of a particular material in the material being grown in accordance with the presence or absence in the reflected beam of scattered incident electrons at a predetermined energy level.

6. The apparatus for analyzing materials claimed in claim 4, wherein the means for analyzing the material further comprises:

means for determining the ratio between materials present in the material being grown in accordance with the ratio in the reflected beam of scattered incident electrons at different predetermined energy levels.

* * * * *